(12) United States Patent
Yamaguchi et al.

(10) Patent No.: US 8,932,833 B2
(45) Date of Patent: Jan. 13, 2015

(54) THERMAL CYCLER AND CONTROL METHOD OF THERMAL CYCLER

(71) Applicant: Seiko Epson Corporation, Tokyo (JP)

(72) Inventors: Akemi Yamaguchi, Matsumoto (JP); Hiroshi Koeda, Suwa (JP)

(73) Assignee: Seiko Epson Corporation (JP)

( * ) Notice: Subject to any disclaimer, the term of this patent is extended or adjusted under 35 U.S.C. 154(b) by 1 day.

(21) Appl. No.: 13/796,498

(22) Filed: Mar. 12, 2013

(65) Prior Publication Data

US 2013/0260421 A1   Oct. 3, 2013

(30) Foreign Application Priority Data

Mar. 30, 2012 (JP) ................................. 2012-079766

(51) Int. Cl.
*C12P 19/34* (2006.01)
*G01N 31/22* (2006.01)

(52) U.S. Cl.
USPC ......................................... 435/91.2; 422/417

(58) Field of Classification Search
USPC ......................................... 435/91.2; 422/417
See application file for complete search history.

(56) References Cited

U.S. PATENT DOCUMENTS

2008/0176290 A1 * 7/2008 Joseph et al. ................ 435/91.2
2012/0122160 A1   5/2012 Saito et al.

FOREIGN PATENT DOCUMENTS

JP   2009-136250   6/2009

* cited by examiner

*Primary Examiner* — Ardin Marschel
(74) *Attorney, Agent, or Firm* — Harness, Dickey & Pierce, P.L.C.

(57) ABSTRACT

An attachment unit for attachment of a reaction container including a channel filled with a reaction solution and a liquid having a specific gravity different from that of the reaction solution and being immiscible with the reaction solution, the reaction solution moving close to opposed inner walls, a first heating unit that heats a first region of the channel and a second heating unit that heats a second region of the channel when the reaction container is attached to the attachment unit, a drive mechanism that switches arrangement of the attachment unit, the first heating unit, and the second heating unit between a first arrangement and a second arrangement in which a lowermost position of the channel is located within a first region and a second region, respectively, and a control unit that controls the drive mechanism, the first heating unit, and the second heating unit are provided.

4 Claims, 10 Drawing Sheets

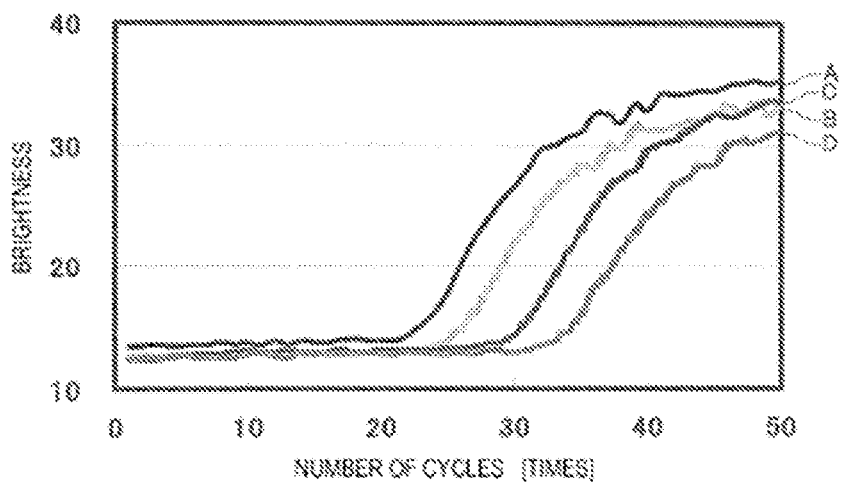

| COMPOSITION | PRESERVATIVE CONCENTRATION | FINAL CONCENTRATION | LIQUID VOLUME [μL] |
|---|---|---|---|
| SuperScript III Platinum | | | 0.2 |
| Buffer | 2x | 1x | 5 |
| F primer | 40μM | 0.8μM | 0.2 |
| R primer | 40μM | 0.8μM | 0.2 |
| Probe | 10μM | 0.2μM | 0.2 |
| Distilled Water | | | 3.2 |
| PLASMID | | | 1 |
| total | | | 10 |

FIG. 9

| Primers and Probes | Sequence | SEQ ID Nos |
|---|---|---|
| InfA F primer | 5'- GAT CRA TCC TGT CAC CTC TGA C -3' | 1 |
| InfA R primer | 5'- AGG GCA TTY TGG ACA AAK CGT CTA -3' | 2 |
| InfA Probe | 5'- TGC AGT CCT CGC TCA CTG GGC ACG -3' | 3 |
| SW InfA F primer | 5'- GCA CGG TCA GCA CTT ATY CTR AG -3' | 4 |
| Sw InfA R primer | 5'- GTG RGC TGG GTT TTC ATT TGG TC 3' | 5 |
| SW InfA Probe | 5'- CYA CTG CAA GCC CAT ACA CAC AAG CAG GCA -3' | 6 |
| SW H1 F primer | 5'- GTG CTA TAA ACA CCA GCC TYC CA -3' | 7 |
| SW H1 R primer | 5'- CGG GAT ATT CCT TAA TCC TGT RGC -3' | 8 |
| SW H1 Probe | 5'- CA GAA TAT ACA TCC RGT CAC AAT TGG ARA A -3' | 9 |
| RNaseP F primer | 5'- AGA TTT GGA CCT GCG AGC G -3' | 10 |
| RNaseP R primer | 5'- GAG CGG CTG TCT CCA CAA GT -3' | 11 |
| RNaseP Probe | 5'- TTC TGA CCT GAA GGC TCT GCG CG -3' | 12 |

| COMPOSITION | PRESERVATIVE CONCENTRATION | FINAL CONCENTRATION | LIQUID VOLUME [uL] |
|---:|---:|---:|---:|
| SuperScript III Platinum | | | 0.2 |
| Buffer | 2x | 1x | 5 |
| F primer | 40uM | 0.8uM | 0.2 |
| R primer | 40uM | 0.8uM | 0.2 |
| Probe | 10uM | 0.2uM | 0.2 |
| Distilled Water | | | 3.2 |
| RNA | | | 1 |
| total | | | 10 |

THERMAL CYCLER AND CONTROL METHOD OF THERMAL CYCLER

BACKGROUND

1. Technical Field

The present invention relates to a thermal cycler and a control method of the thermal cycler.

2. Related Art

Recently, with development of utilization technologies of genes, medical treatment utilizing genes such as gene diagnoses and gene therapies has attracted attention, and many techniques using genes for breed identification and breed improvement have been developed in agriculture and livestock fields. As technologies for utilizing genes, a technology such as a PCR (Polymerase Chain Reaction) method has been widespread. Today, the PCR method is an essential technology in elucidation of information of biological materials.

The PCR method is a technique of amplifying target nucleic acid by applying thermal cycling to a solution containing nucleic acid as a target of amplification (target nucleic acid) and reagent (reaction solution). The thermal cycling is processing of periodically applying two or more steps of temperatures to the reaction solution. In the PCR method, generally, thermal cycling of two or three steps is applied.

In the PCR method, generally, a container for biochemical reaction called a tube or a chip for biological sample reaction (biochip) is used. However, in the technique of related art, there have been problems that large amounts of reagent etc. are necessary, equipment becomes complex for realization of thermal cycling necessary for reaction, and the reaction takes time. Accordingly, biochips and reactors for performing PCR with high accuracy in short time using extremely small amounts of reagent and specimen have been required.

In order to solve the problem, Patent Document 1 (JP-A-2009-136250) has disclosed a biological sample reactor of performing thermal cycling by rotating a chip for biological sample reaction filled with a reaction solution and a liquid being immiscible with the reaction solution and having a lower specific gravity than that of the reaction solution around a rotation axis in the horizontal direction to move the reaction solution.

Further, for improvement in accuracy of amplification in PCR, PCR including a step of hot start of activating enzyme used for PCR (PCR enzyme) with heat has been known.

The equipment disclosed in Patent Document 1 has applied thermal cycling to a reaction solution by continuously rotating a biochip. However, additional ideas have been required for holding the reaction solution at a desired temperature in a desired period and realizing PCR including a step of hot start or the like different from those of thermal cycling of normal PCR because the reaction solution moves within a channel of the biochip with the rotation.

SUMMARY

An advantage of some aspects of the invention is to provide a thermal cycler and a control method of thermal cycler suitable for PCR including hot start.

(1) A thermal cycler according to an aspect of the invention includes an attachment unit for attachment of a reaction container including a channel filled with a reaction solution containing hot start PCR enzyme and a liquid having a specific gravity different from that of the reaction solution and being immiscible with the reaction solution, the reaction solution moving close to opposed inner walls, a first heating unit that heats a first region of the channel when the reaction container is attached to the attachment unit, a second heating unit that heats a second region of the channel different from the first region when the reaction container is attached to the attachment unit, a drive mechanism that switches arrangement of the attachment unit, the first heating unit, and the second heating unit between a first arrangement in which a lowermost position of the channel in a direction in which gravity acts is located within the first region and a second arrangement in which the lowermost position of the channel in the direction in which the gravity acts is located within the second region when the reaction container is attached to the attachment unit, and a control unit that controls the drive mechanism, the first heating unit, and the second heating unit, wherein the control unit performs first processing of controlling the first heating unit at a first temperature, second processing of controlling the second heating unit at a second temperature higher than the first temperature, third processing of allowing a first period to elapse with the arrangement of the attachment unit, the first heating unit, and the second heating unit being the second arrangement after the second processing, and fourth processing of controlling the drive mechanism to switch the arrangement of the attachment unit, the first heating unit, and the second heating unit from the second arrangement to the first arrangement if a second period has elapsed with the arrangement of the attachment unit, the first heating unit, and the second heating unit being the second arrangement after the first processing and the third processing.

According to the aspect of the invention, the state in which the reaction container is held in the first arrangement and the state in which the reaction container is held in the second arrangement may be switched by switching the arrangement of the attachment unit, the first heating unit, and the second heating unit. The first arrangement is the arrangement in which the first region of the channel forming the reaction container is located in the lowermost part of the channel in the direction in which the gravity acts. The second arrangement is the arrangement in which the second region of the channel forming the reaction container is located in the lowermost part of the channel in the direction in which the gravity acts. That is, when the specific gravity of the reaction solution is relatively large, the reaction solution may be held in the first region in the first arrangement and the reaction solution may be held in the second region in the second arrangement by the action of the gravity. The first region is heated by the first heating unit and the second region is heated by the second heating unit, and thereby, the first region and the second region may be set at different temperatures. Therefore, the reaction solution may be held at a predetermined temperature while the reaction container is held in the first arrangement or the second arrangement, and the thermal cycler that can easily control the heating period may be provided. Further, the reaction solution is held at the second temperature in the third processing and the fourth processing, and the reaction solution is held at the first temperature lower than the second temperature after the fourth processing. When the thermal cycler is applied to PCR, the first temperature corresponds to an annealing and elongation temperature and the second temperature corresponds to a denaturation temperature of DNA. Generally, the temperature at which the PCR enzyme is activated is nearly equal to the denaturation temperature. Therefore, by performing the third processing, thermal cycling that enables hot start of PCR may be realized in addition to the thermal cycling of normal PCR.

(2) In the above described thermal cycler, the control unit may perform fifth processing of controlling the drive mechanism to switch the arrangement of the attachment unit, the first heating unit, and the second heating unit from the first arrangement to the second arrangement and the forth processing repeatedly at a predetermined number of times if a third period has elapsed with the arrangement of the attachment unit, the first heating unit, and the second heating unit being the first arrangement after the fourth processing.

The reaction solution is held at the second temperature until the second period has elapsed in the second arrangement in the fourth processing, and the reaction solution is held at the first temperature until the third period has elapsed in the first arrangement in the fifth processing. Therefore, thermal cycling suitable for PCR may be performed repeatedly at a predetermined number of times.

(3) In the above described thermal cycler, the control unit may further perform sixth processing of controlling the first heating unit at a third temperature lower than the first temperature and allowing a fourth period to elapse with the arrangement of the attachment unit, the first heating unit, and the second heating unit being the first arrangement, seventh processing of controlling the drive mechanism to switch the arrangement of the attachment unit, the first heating unit, and the second heating unit from the first arrangement to the second arrangement after the sixth processing and the second processing, and third processing after the seventh processing.

The reaction solution is held at the third temperature lower than the first temperature in the seventh processing. The third temperature may be set to a temperature at which reverse transcription reaction progresses in RT-PCR (reverse transcription polymerase chain reaction). Therefore, by performing the seventh processing prior to the third processing, the reverse transcription reaction may be performed before PCR, and thus, the thermal cycler suitable for RT-PCR may be realized.

(4) A control method of a thermal cycler according to an aspect of the invention is a control method of a thermal cycler, and the thermal cycler includes an attachment unit for attachment of a reaction container including a channel filled with a reaction solution containing hot start PCR enzyme and a liquid having a specific gravity different from that of the reaction solution and being immiscible with the reaction solution, the reaction solution moving close to opposed inner walls, a first heating unit that heats a first region of the channel when the reaction container is attached to the attachment unit, a second heating unit that heats a second region of the channel different from the first region when the reaction container is attached to the attachment unit, and a drive mechanism that switches arrangement of the attachment unit, the first heating unit, and the second heating unit between a first arrangement in which a lowermost position of the channel in a direction in which gravity acts is located within the first region and a second arrangement in which the lowermost position of the channel in the direction in which the gravity acts is located within the second region when the reaction container is attached to the attachment unit, and the control method includes performing first processing of controlling the first heating unit at a first temperature, performing second processing of controlling the second heating unit at a second temperature higher than the first temperature, performing third processing of allowing a first period to elapse with the arrangement of the attachment unit, the first heating unit, and the second heating unit being the second arrangement, and performing fourth processing of controlling the drive mechanism to switch the arrangement of the attachment unit, the first heating unit, and the second heating unit from the second arrangement to the first arrangement if a second period has elapsed with the arrangement of the attachment unit, the first heating unit, and the second heating unit being the second arrangement after the third processing.

According to the aspect of the invention, the state in which the reaction container is held in the first arrangement and the state in which the reaction container is held in the second arrangement may be switched by switching the arrangement of the attachment unit, the first heating unit, and the second heating unit. The first arrangement is the arrangement in which the first region of the channel forming the reaction container is located in the lowermost part of the channel in the direction in which the gravity acts. The second arrangement is the arrangement in which the second region of the channel forming the reaction container is located in the lowermost part of the channel in the direction in which the gravity acts. That is, when the specific gravity of the reaction solution is relatively large, the reaction solution may be held in the first region in the first arrangement and the reaction solution may be held in the second region in the second arrangement by the action of the gravity. The first region is heated by the first heating unit and the second region is heated by the second heating unit, and thereby, the first region and the second region may be set at different temperatures. Therefore, the reaction solution may be held at a predetermined temperature while the reaction container is held in the first arrangement or the second arrangement, and the control method of the thermal cycler that can easily control the heating period may be provided. Further, the reaction solution is held at the second temperature in the third processing and the fourth processing, and the reaction solution is held at the first temperature lower than the second temperature after the fourth processing. When the thermal cycler is applied to PCR, the first temperature corresponds to the annealing and elongation temperature and the second temperature corresponds to the denaturation temperature of DNA. Generally, the temperature at which the PCR enzyme is activated is nearly equal to the denaturation temperature. Therefore, by performing the third processing, thermal cycling that enables hot start of PCR may be realized in addition to the thermal cycling of normal PCR.

BRIEF DESCRIPTION OF THE DRAWINGS

The invention will be described with reference to the accompanying drawings, wherein like numbers reference like elements.

FIG. 9 is a table showing a composition of a reaction solution 140 in a first working example.

FIG. 10 is a table showing base sequences of forward primers (F primers), reverse primers (R primers), and probes.

FIG. 11 is a graph showing relationships between the number of cycles of thermal cycling processing and measured brightness in the first working example.

DESCRIPTION OF EXEMPLARY EMBODIMENTS

As below, preferred embodiments of the invention will be explained in detail using the drawings. Note that the embodiments to be explained do not unduly limit the invention described in the appended claims. Further, not all of the configurations to be explained are essential component elements of the invention.

1. Overall Configuration of Thermal Cycler According to Embodiment

Figure 1:
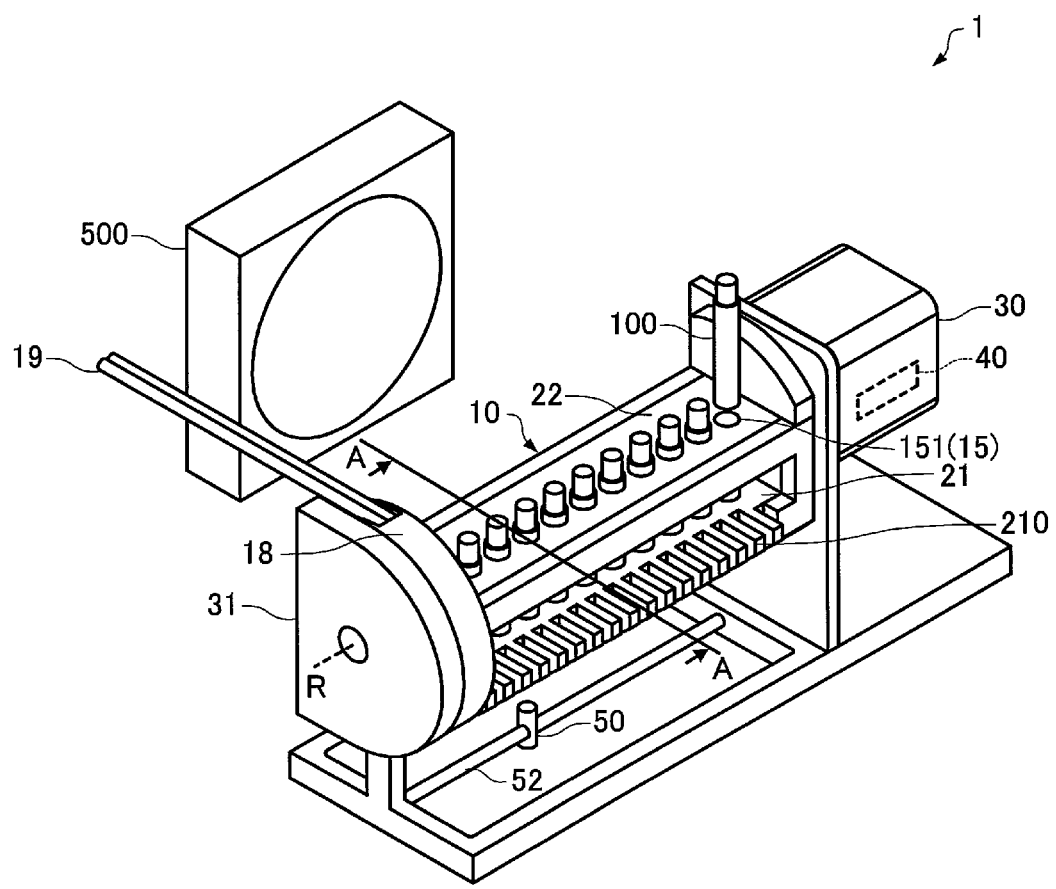
FIG. 1 is a perspective view of a thermal cycler 1 according to an embodiment.
Figure 2:
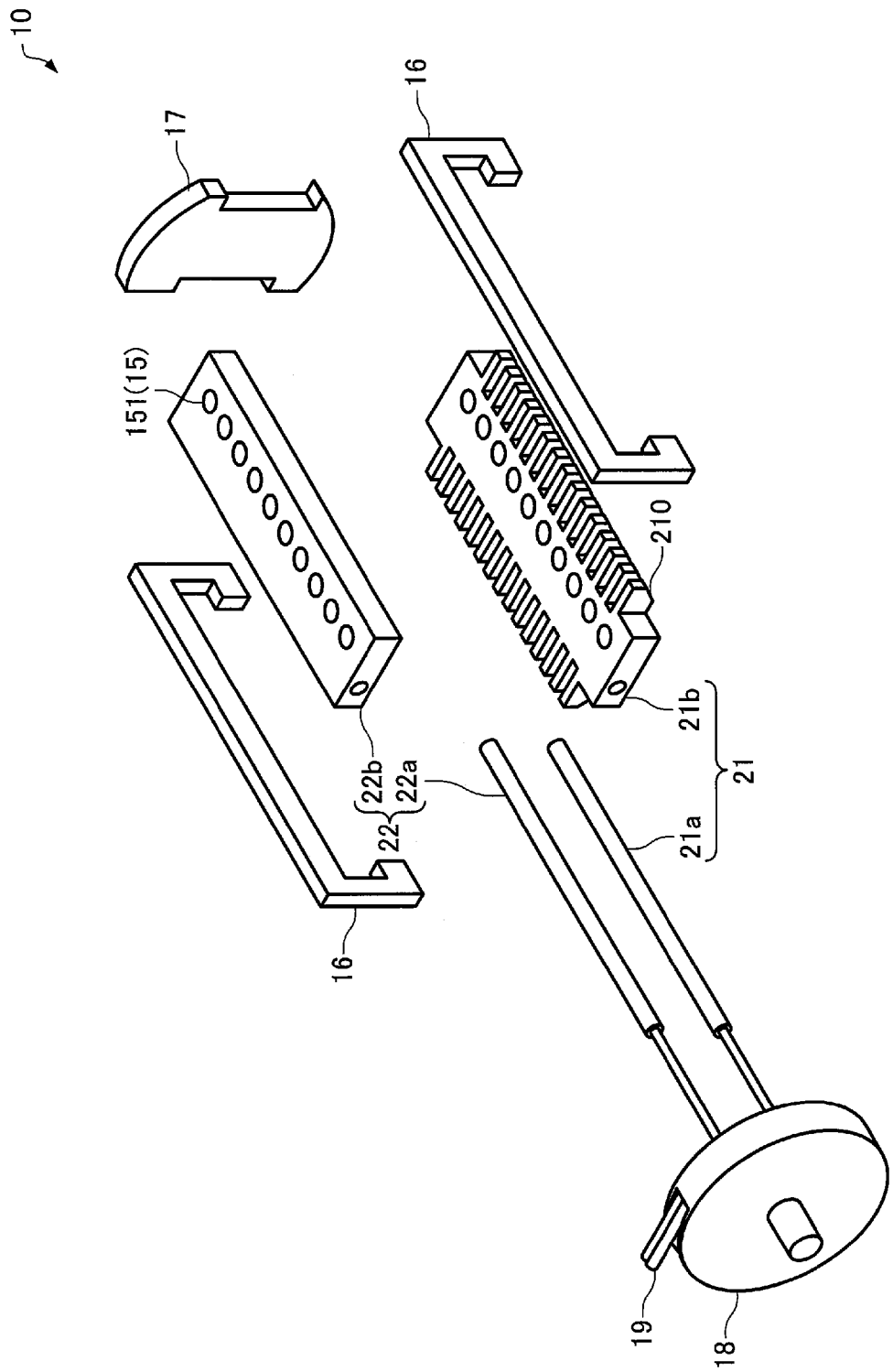
FIG. 2 is an exploded perspective view of a main body 10 of the thermal cycler 1 according to the embodiment.
Figure 3:
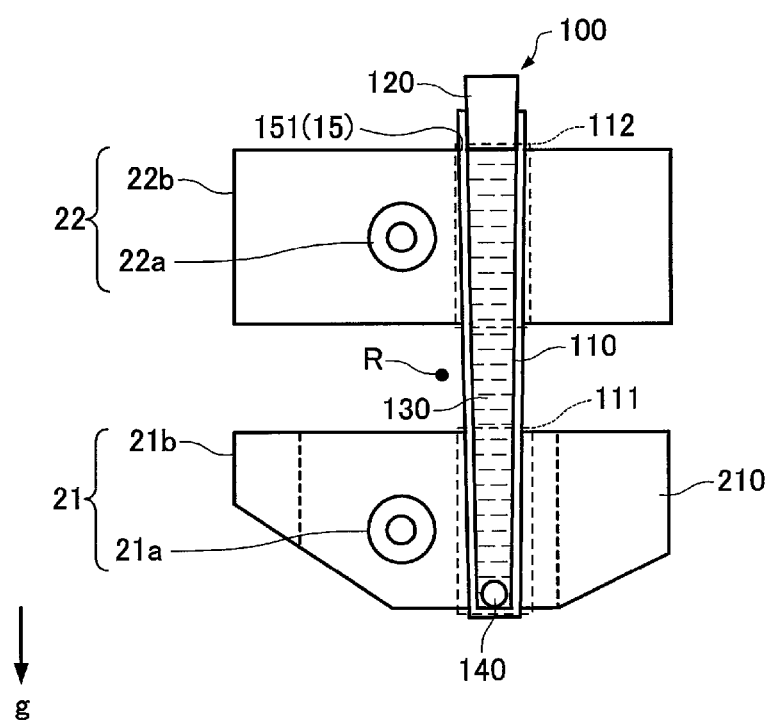
FIG. 3 is a vertical sectional view along A-A line in FIG. 1.

FIG. 1 is a perspective view of a thermal cycler 1 according to an embodiment. FIG. 2 is an exploded perspective view of a main body 10 of the thermal cycler 1 according to the embodiment. FIG. 3 is a vertical sectional view along A-A line in FIG. 1. In FIG. 3, arrow g indicates a direction in which gravity acts.

The thermal cycler 1 according to the embodiment includes an attachment unit 15 for attachment of a reaction container 100 including a channel 110 filled with a reaction solution 140 containing hot start PCR enzyme and a liquid 130 having a specific gravity different from that of the reaction solution 140 and being immiscible with the reaction solution 140, the reaction solution 140 moving close to opposed inner walls (the details will be described later in section of "2. Configuration of Reaction Container attached to Thermal Cycler according to Embodiment"), a first heating unit 21 that heats a first region 111 of the channel 110 when the reaction container 100 is attached to the attachment unit 15, a second heating unit 22 that heats a second region 112 of the channel 110 different from the first region 111 when the reaction container 100 is attached to the attachment unit 15, a drive mechanism 30 that switches arrangement of the attachment unit 15, the first heating unit 21, and the second heating unit 22 between a first arrangement in which the lowermost position of the channel 110 in a direction in which gravity acts is located within the first region 111 and a second arrangement in which the lowermost position of the channel 110 in the direction in which the gravity acts is located within the second region 112 when the reaction container 100 is attached to the attachment unit 15, and a control unit 40 that controls the drive mechanism 30, the first heating unit 21, and the second heating unit 22.

In the example shown in FIG. 1, the thermal cycler 1 includes the main body 10 and the drive mechanism 30. As shown in FIG. 2, the main body 10 includes the attachment unit 15, the first heating unit 21, and the second heating unit 22.

The attachment unit 15 has a structure to which the reaction container 100 is attached. In the example shown in FIGS. 1 and 2, the attachment unit 15 of the thermal cycler 1 has a slot structure with an insertion opening 151 into which the reaction container 100 is attached by insertion from the insertion opening 151. In the example shown in FIG. 2, the attachment unit 15 has a structure in which the reaction container 100 is inserted into a hole penetrating a first heat block 21b of the first heating unit 21 and a second heat block 22b of the second heating unit 22. The first heat block 21b and the second heat block 22b will be described later. A plurality of the attachment units 15 may be provided in the main body 10, and ten attachment units 15 are provided in the main body 10 in the example shown in FIGS. 1 and 2. Further, in the example shown in FIGS. 2 and 3, the attachment unit 15 is formed as a part of the first heating unit 21 and the second heating unit 22, however, the attachment unit 15 and the first heating unit 21 and the second heating unit 22 may be formed as separate members as long as the positional relationship between them may not change when the drive mechanism 30 is operated.

Note that, in the embodiment, the example in which the attachment unit 15 has the slot structure has been shown, however, the attachment unit 15 has any structure as long as it may hold the reaction container 100. For example, a structure of fitting the reaction container 100 in a recess that conforms to the shape of the reaction container 100 or a structure of sandwiching and holding the reaction container 100 may be employed.

The first heating unit 21 heats the first region 111 of the channel 110 of the reaction container 100 when the reaction container 100 is attached to the attachment unit 15. In the example shown in FIG. 3, the first heating unit 21 is located in a position for heating the first region 111 of the reaction container 100 in the main body 10.

The first heating unit 21 may include a mechanism of generating heat and a member of transmitting the generated heat to the reaction container 100. In the example shown in FIG. 2, the first heating unit 21 includes a first heater 21a as a mechanism of generating heat and the first heat block 21b as a member of transmitting the generated heat to the reaction container 100.

In the thermal cycler 1, the first heater 21a is a cartridge heater and connected to an external power supply (not shown) by a conducting wire 19. The first heater 21a is not limited but includes a carbon heater, a sheet heater, an IH heater (electromagnetic induction heater), a Peltier device, a heating liquid, a heating gas, etc. The first heater 21a is inserted into the first heat block 21b and the first heater 21a generates heat to heat the first heat block 21b. The first heat block 21b is a member of transmitting the heat generated from the first heater 21a to the reaction container 100. In thermal cycler 1, the first heat block 21b is an aluminum block. The cartridge heater is easily temperature-controlled, and, with the cartridge heater for the first heater 21a, the temperature of the first heating unit 21 may be easily stabilized. Therefore, more accurate thermal cycling may be realized.

The material of the heat block may be appropriately selected in consideration of conditions of coefficient of thermal conductivity, heat retaining characteristics, ease of working, etc. For example, aluminum has a high coefficient of thermal conductivity, and, by forming the first heat block 21b using aluminum, the reaction container 100 may be efficiently heated. Further, unevenness in heating is hard to be produced in the heat block, and the thermal cycling with high accuracy may be realized. Furthermore, working is easy, and the first heat block 21b may be molded with high accuracy and the heating accuracy may be improved. Therefore, more accurate thermal cycling may be realized. Note that, for the material of the heat block, for example, copper alloy may be used or several materials may be combined.

It is preferable that the first heating unit 21 is in contact with the reaction container 100 when the attachment unit 15 is attached to the reaction container 100. Thereby, when the reaction container 100 is heated by the first heating unit 21, the heat of the first heating unit 21 may be transmitted to the reaction container 100 more stably than in the configuration in which the first heating unit 21 is not in contact with the reaction container 100, and thus, the temperature of the reaction container 100 may be stabilized. When the attachment unit 15 is formed as the part of the first heating unit 21 like in the embodiment, it is preferable that the attachment unit 15 is in contact with the reaction container 100. Thereby, the heat of the first heating unit 21 may be stably transmitted to the reaction container 100, and the reaction container 100 may be efficiently heated.

The second heating unit 22 heats the second region 112 of the channel 110 of the reaction container 100 nearer the insertion opening 151 than the first region 111 to a second temperature different from the first temperature when the attachment unit 15 is attached to the reaction container 100. In the example shown in FIG. 3, the second heating unit 22 is located in a position for heating the second region 112 of the reaction container 100 in the main body 10. The second heating unit 22 includes a second heater 22$a$ and a second heat block 22$b$. The configuration of the second heating unit 22 in the embodiment is the same as that of the first heating unit 21 except that the region of the reaction container 100 to be heated and the temperature of heating are different from those of the first heating unit 21. Note that different heating mechanisms may be employed in the first heating unit 21 and the second heating unit 22. Further, the materials of the first heat block 21$b$ and the second heat block 22$b$ may be different.

The first heating unit 21 and the second heating unit 22 function as a temperature gradient forming section of forming a temperature gradient in a direction in which the reaction solution 140 moves for the channel 110 when the attachment unit 15 is attached to the reaction container 100. Here, "forming a temperature gradient" refers to forming a state in which a temperature changes along a predetermined direction. Therefore, "forming a temperature gradient in a direction in which the reaction solution 140 moves" refers to forming a state in which a temperature changes in a direction in which the reaction solution 140 moves. "A state in which a temperature changes along a predetermined direction" may refer to a state in which a temperature monotonically becomes higher or lower along a predetermined direction, or a state in which a temperature change is changed in the middle from the change to be higher to the change to be lower or from the change to be lower to the change to be higher along a predetermined direction. In the main body 10 of the thermal cycler 1, the first heating unit 21 is located at the side farther from the insertion opening 151 of the attachment unit 15 and the second heating unit 22 is located at the side nearer the insertion opening 151 of the attachment unit 15.

Further, the first heating unit 21 and the second heating unit 22 are provided separately from each other in the main body 10. Thereby, the first heating unit 21 and the second heating unit 22 controlled at the different temperatures from each other are hard to affect each other, and the temperatures of the first heating unit 21 and the second heating unit 22 may be easily stabilized. A spacer may be provided between the first heating unit 21 and the second heating unit 22. In the main body 10 of the thermal cycler 1, the first heating unit 21 and the second heating unit 22 are fixed on their peripheries by a fixing member 16, a flange 17, and a flange 18. The flange 18 is supported by a bearing 31. Note that the number of heating units may be an arbitrary number equal to or more than two as long as the temperature gradient is formed to a degree that may secure desired reaction accuracy.

The temperatures of the first heating unit 21 and the second heating unit 22 may be controlled by a temperature sensor (not shown) and the control unit 40 to be described later. It is preferable that the temperatures of the first heating unit 21 and the second heating unit 22 are set so that the reaction container 100 may be heated to a desired temperature. The details of the control of the temperatures of the first heating unit 21 and the second heating unit 22 will be described in the section of "3. Control Example of Thermal Cycler". Note that it is only necessary that the temperatures of the first heating unit 21 and the second heating unit 22 are controlled so that the first region 111 and the second region 112 of the reaction container 100 may be heated to desired temperatures. For example, in consideration of the material and the size of the reaction container 100, the temperatures of the first region 111 and the second region 112 may be heated to the desired temperatures more accurately. In the embodiment, the temperatures of the first heating unit 21 and the second heating unit 22 are measured by a temperature sensor. The temperature sensor of the embodiment is a thermocouple. Note that the temperature sensor is not limited but may include a temperature sensing resistor or a thermistor, for example.

The drive mechanism 30 switches the arrangement of the attachment unit 15, the first heating unit 21, and the second heating unit 22 between the first arrangement in which the lowermost position of the channel 110 in the direction in which the gravity acts is located within the first region 111 and the second arrangement in which the lowermost position of the channel 110 in the direction in which the gravity acts is located within the second region 112 when the reaction container 100 is attached to the attachment unit 15. In the embodiment, the drive mechanism 30 is a mechanism of rotating the attachment unit 15, the first heating unit 21, and the second heating unit 22 around the rotation axis R having a component perpendicular to the direction in which the gravity acts and a component perpendicular to the direction in which the reaction solution 140 moves in the channel 110 when the attachment unit 15 is attached to the reaction container 100.

The direction "having a component perpendicular to the direction in which the gravity acts" refers to a direction having a component perpendicular to the direction in which the gravity acts when the direction is expressed by a vector sum of "a component in parallel to the direction in which the gravity acts" and "a component perpendicular to the direction in which the gravity acts".

The direction "having a component perpendicular to the direction in which the reaction solution 140 moves in the channel 110" refers to a direction having a component perpendicular to the direction in which the reaction solution 140 moves in the channel 110 when the direction is expressed by a vector sum of "a component in parallel to the direction in which the reaction solution 140 moves in the channel 110" and "a component perpendicular to the direction in which the reaction solution 140 moves in the channel 110".

In the thermal cycler 1 of the embodiment, the drive mechanism 30 rotates the attachment unit 15, the first heating unit 21, and the second heating unit 22 around the same rotation axis R. Further, in the embodiment, the drive mechanism 30 includes a motor and a drive shaft (not shown), and the drive shaft and the flange 17 of the main body 10 are connected. When the motor of the drive mechanism 30 is operated, the main body 10 is rotated around the drive axis as the rotation axis R. In the embodiment, ten attachment units 15 are provided along the direction of the rotation axis R.

Note that, as the drive mechanism 30, not limited to the motor, but, for example, a handle, a spiral spring, or the like may be employed.

The thermal cycler 1 may include a measurement unit 50. The measurement unit 50 measures intensity of light having a predetermined wavelength. In the embodiment, a fluorescence detector is employed as the measurement unit 50. Thereby, for example, if a fluorescent probe that changes intensity of light having a predetermined wavelength by complementary binding to specific DNA is contained in the reaction solution 140, the thermal cycler 1 may be used for application with fluorescence measurement such as real-time PCR. The number of measurement units 50 is arbitrary as long as the measurement may be performed without difficulty. In the example shown in FIG. 1, the fluorescence measurement is performed while one measurement unit 50 is moved along a slide 52.

It is more preferable that the measurement unit 50 is located at the side nearer the first heating unit 21 than at the side nearer the second heating unit 22. Thereby, the measurement unit hardly becomes an obstacle to the operation when the attachment unit 15 is attached to the reaction container 100. Further, the measurement unit 50 may be provided to measure light from a region containing the first region 111 of the reaction container 100. When the temperature of the first heating unit 21 is set to an annealing and elongation temperature (a temperature at which annealing and elongation reaction progresses) of PCR, the intensity of the light having the predetermined wavelength correlated with an amount of specific DNA may be measured more accurately. Therefore, appropriate fluorescence measurement may be performed in real-time PCR. Furthermore, when a reaction container 100 with a lid (sealing part 120) to be described later is used, more appropriate fluorescence measurement may be performed in the first region 111 at the side farther from the lid than in the second region 112 at the side nearer the lid because there are less members between the measurement unit 50 and the reaction solution 140.

As described above, when the thermal cycler 1 is used for real-time PCR, in a period in which thermal cycling necessary for PCR is applied to the reaction solution 140, it is preferable that the measurement unit 50 is provided at the side nearer the first heating unit 21 and the first heating unit 21 is set to the annealing and elongation temperature of PCR (about 50° C. to 75° C.). In this case, the second heating unit 22 nearer the insertion opening 151 is set to a thermal denaturation temperature (about 90° C. to 100° C.) higher than the annealing and elongation temperature of PCR.

The thermal cycler 1 includes the control unit 40. The control unit 40 controls the first heating unit 21, the second heating unit 22, and the drive mechanism 30. The control unit 40 may further control the measurement unit 50. A control example by the control unit 40 will be described in detail in the section of "3. Control Example of Thermal Cycler". The control unit 40 may be adapted to be realized by a dedicated circuit and perform the control to be described later. Further, the control unit 40 may be adapted to function as a computer using a CPU (Central Processing Unit), for example, by executing control programs stored in a memory device such as a ROM (Read Only Memory) or a RAM (Random Access Memory) and perform the control to be described later. In this case, the memory device may have a work area that temporarily stores intermediate data and control results with the control. Further, the control unit 40 may have a timer for measuring time. Furthermore, the control unit 40 may control the first heating unit 21 and the second heating unit 22 to desired temperatures based on the output of the above described temperature sensor (not shown).

It is preferable that the thermal cycler 1 includes a structure of holding the reaction container 100 in a predetermined position with respect to the first heating unit 21 and the second heating unit 22. Thereby, a predetermined regions of the reaction container 100 may be heated by the first heating unit 21 and the second heating unit 22. More specifically, the first region 111 and the second region 112 of the channel 110 forming the reaction container 100 may be heated by the first heating unit 21 and the second heating unit 22, respectively. In the embodiment, by appropriately setting the sizes of through holes provided in the first heat block 21b and the second heat block 22b (the diameter of the attachment unit 15), the reaction container 100 may be held in a predetermined position with respect to the first heating unit 21 and the second heating unit 22.

The first heat block 21b may have a structure with fins 210. Thereby, the surface area of the first heating unit becomes larger and the time taken for changing the temperature of the first heating unit 21 from the higher temperature to the lower temperature becomes shorter.

The thermal cycler 1 may include a fan 500 that blows air to the first heating unit 21 and the second heating unit 22. By blowing air, the heat transfer between the first heating unit 21 and the second heating unit 22 may be suppressed. Therefore, the first heating unit 21 and the second heating unit 22 controlled at the different temperatures from each other become harder to affect each other, and thus, the temperatures of the first heating unit 21 and the second heating unit 22 may be easily stabilized.

Figure 4:
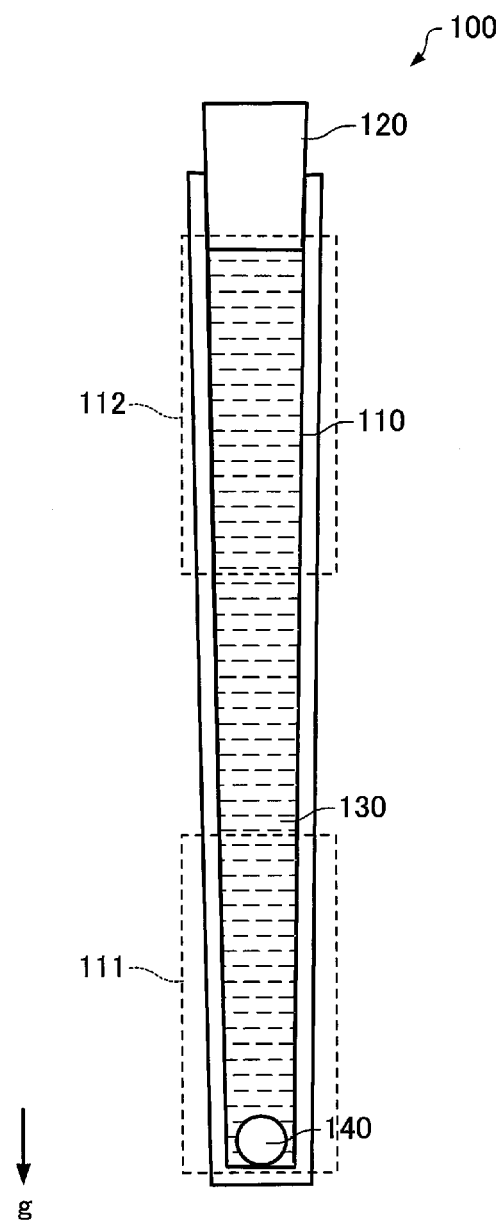
FIG. 4 is a sectional view showing a configuration of a reaction container 100 to be attached to the thermal cycler 1 according to the embodiment.

2. Configuration of Reaction Container Attached to Thermal Cycler According to Embodiment FIG. 4 is a sectional view showing a configuration of the reaction container 100 attached to the thermal cycler 1 according to the embodiment. In FIG. 4, arrow g indicates a direction in which gravity acts.

The reaction container 100 includes the channel 110 filled with the reaction solution 140 containing hot start PCR enzyme and a liquid 130 having a different specific gravity from that of the reaction solution 140 and being immiscible with the reaction solution 140 (hereinafter, referred to as "liquid 130"), in which the reaction solution 140 moves along the opposed inner walls. In the embodiment, the liquid 130 is a liquid having a lower specific gravity than that of the reaction solution 140 and being immiscible with the reaction solution 140. The hot start PCR enzyme refers to PCR enzyme having enzyme activity increased (activated) in a predetermined temperature environment. Generally, the temperature at which the hot start enzyme is activated is higher than the room temperature and nearly equal to the denaturation temperature of DNA. For the hot start PCR enzyme, known enzyme may be used and, for example, Taq polymerase ("Taq" is a registered trademark) for hot start and hot start PCR enzyme having activity suppressed by antibody or the like may be used. Note that, as the liquid 130, for example, a liquid being immiscible with the reaction solution 140 and having a higher specific gravity than that of the reaction solution 140 may be employed. In the example shown in FIG. 4, the reaction container 100 includes the channel 110 and the sealing part 120. The channel 110 is filled with the reaction solution 140 and the liquid 130, and sealed by the sealing part 120.

The channel 110 is formed so that the reaction solution 140 may move along the opposed inner walls. Here, "opposed inner walls" of the channel 110 refer to two regions having an opposed positional relationship on the wall surfaces of the channel 110. "Along" refers to a state in which a distance from the reaction solution 140 to the wall surface of the channel 110 is short, and includes a state in which the reaction solution 140 is in contact with the wall surface of the channel 110. Therefore, "the reaction solution 140 moves along the opposed inner walls" refers to "the reaction solution 140 moves in a state in which the distances from the wall surface of the channel 110 to both two regions in the opposed positional relationship are short". In other words, the distance between the opposed two inner walls of the channel 110 is a distance to a degree that the reaction solution 140 moves along the inner walls.

When the channel 110 of the reaction container 100 has the above described shape, the direction in which the reaction solution 140 moves within the channel 110 may be regulated, and thus, the path in which the reaction solution 140 moves within the channel 110 may be defined to some degree. Thereby, the time taken for the reaction solution 140 to move within the channel 110 may be restricted within a certain range. Therefore, it is preferable that the distance between the opposed two inner walls of the channel 110 is a distance to a degree at which variations in thermal cycling conditions applied to the reaction solution 140 produced by variations in time for the reaction solution 140 to move within the channel 110 may satisfy desired accuracy, i.e., a degree at which the reaction result may satisfy desired accuracy. More specifically, it is desirable that the distance in the direction perpendicular to the direction in which the reaction solution 140 between the opposed two inner walls of the channel 110 moves is a distance to a degree not exceeding two or more droplets of the reaction solution 140.

In the example shown in FIG. 4, the outer shape of the reaction container 100 is a circular truncated cone shape, and the channel 110 in the direction along the center axis (the vertical direction in FIG. 4) as the longitudinal direction is formed. The shape of the channel 110 is a circular truncated cone shape with a section in the direction perpendicular to the longitudinal direction of the channel 110, i.e., a section perpendicular to the direction in which the reaction solution 140 moves in a certain region of the channel 110 (this refers to "section" of the channel 110) in a circular shape. Therefore, in the reaction container 100, the opposed inner walls of the channel 110 are regions containing two points on the wall surface of the channel 110 opposed with the center of the section of the channel 110 in between. Further, "the direction in which the reaction solution 140 moves" is the longitudinal direction of the channel 110.

Note that the shape of the channel 110 is not limited to the truncated cone shape, but may be a columnar shape, for example. Further, the section shape of the channel 110 is not limited to the circular shape, but may be any of a polygonal shape or an oval shape as long as the reaction solution 140 may move along the opposed inner walls. For example, when the section of the channel 110 of the reaction container 100 has a polygonal shape, if a channel having a circular section inscribed in the channel 110 is assumed, "opposed inner walls" are opposed inner walls of the channel. That is, it is only necessary that the channel 110 is formed so that the reaction solution 140 may move along opposed inner walls of a virtual channel having a circular section inscribed in the channel 110. Thereby, even when the section of the channel 110 has a polygonal shape, a path in which the reaction solution 140 moves between the first region 111 and the second region 112 may be defined to some degree. Therefore, the time taken for the reaction solution 140 to move between the first region 111 and the second region 112 may be restricted within a certain range.

The first region 111 of the reaction container 100 is a partial region of the channel 110 to be heated by the first heating unit 21. The second region 112 is a partial region of the channel 110 different from the first region 111 to be heated by the second heating unit 22. In the example shown in FIG. 4, the first region 111 is a region containing one end part in the longitudinal direction of the channel 110, and the second region 112 is a region containing the other end part in the longitudinal direction of the channel 110. In the example shown in FIG. 4, the region surrounded by a dotted line containing the end part at the side farther from the sealing part 120 of the channel 110 is the first region 111, and the region surrounded by a dotted line containing the end part at the side nearer the sealing part 120 of the channel 110 is the second region 112. In the thermal cycler 1 according to the embodiment, the first heating unit 21 heats the first region 111 of the reaction container 100 and the second heating unit 22 heats the second region 112 of the reaction container 100, and thereby, a temperature gradient is formed in the direction in which the reaction solution 140 moves with respect to the channel 110 of the reaction container 100.

The channel 110 is filled with the liquid 130 and the reaction solution 140. The liquid 130 has a property of being immiscible, i.e., unmixed with the reaction solution 140, and the reaction solution 140 is held in droplets in the liquid 130 as shown in FIG. 4. The reaction solution 140 has the higher specific gravity than that of the liquid 130 and is located in the lowermost region of the channel 110 in the direction in which the gravity acts. As the liquid 130, for example, dimethyl silicone oil or paraffin oil may be used. The reaction solution 140 is a liquid containing components necessary for reaction. For example, when the reaction is PCR including hot start, the reaction solution 140 contains DNA to be amplified, hot start DNA polymerase necessary for amplification of the DNA (hot start PCR enzyme), primer, a fluorescent probe that changes intensity of light having a predetermined wavelength by complementary binding to specific DNA, etc. Further, for example, when the reaction is RT-PCR including hot start, the reaction solution 140 contains reverse transcriptase enzyme, RNA as a template of reverse transcription, hot start DNA polymerase necessary for amplification of the reverse transcribed cDNA (hot start PCR enzyme), primer, a fluorescent probe that changes intensity of light having a predetermined wavelength by complementary binding to specific DNA, etc. For example, when PCR is performed using an oil as the liquid 130, it is preferable that the reaction solution 140 is a solution containing the above described components.

3. Control Example of Thermal Cycler

Figure 5:
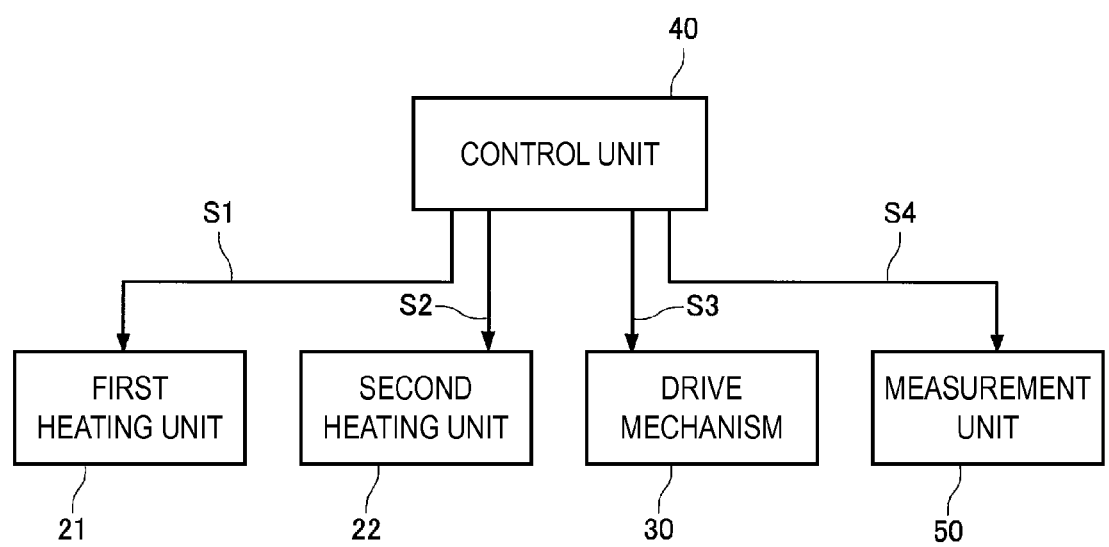
FIG. 5 is a functional block diagram of the thermal cycler 1 according to the embodiment.

FIG. 5 is a functional block diagram of the thermal cycler 1 according to the embodiment. The control unit 40 controls the temperature of the first heating unit 21 by outputting a control signal S1 to the first heating unit 21. The control unit 40 controls the temperature of the second heating unit 22 by outputting a control signal S2 to the second heating unit 22. The control unit 40 controls the drive mechanism 30 by outputting a control signal S3 to the drive mechanism 30. The control unit 40 controls the measurement unit 50 by outputting a control signal S4 to the measurement unit 50.

Next, a control example of the thermal cycler 1 according to the embodiment will be explained. As below, control of rotating the attachment unit 15, the first heating unit 21, and the second heating unit 22 between the first arrangement in which the lowermost position of the channel 110 in the direction in which the gravity acts is located within the first region 111 and the second arrangement in which the lowermost position of the channel 110 in the direction in which the gravity acts is located within the second region 112 when the reaction container 100 is attached to the attachment unit 15 will be explained as an example.

Figure 6A:
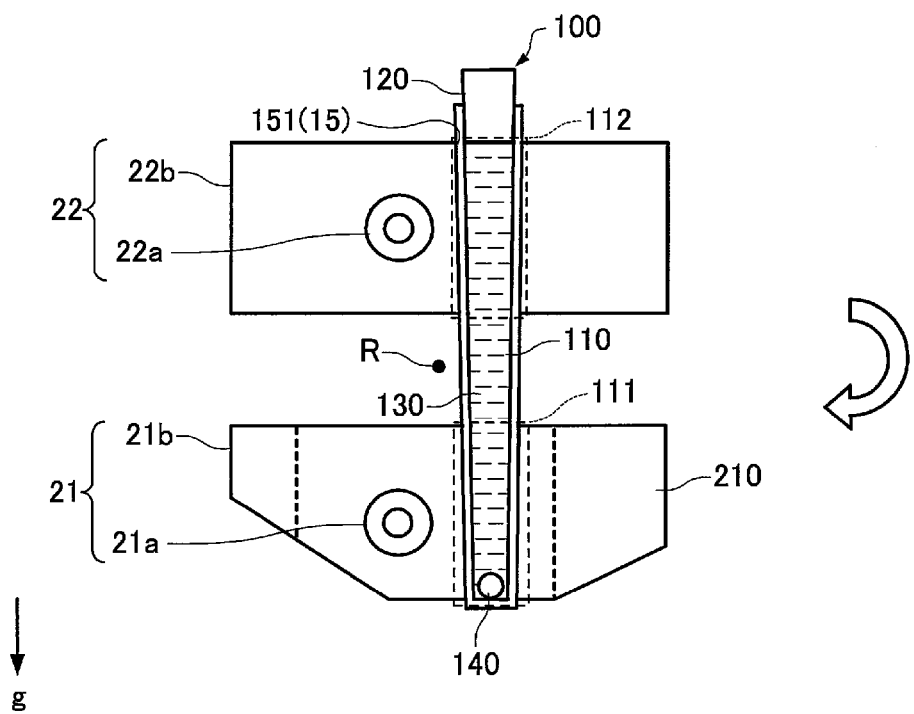
FIG. 6A is a sectional view schematically showing a section in a plane passing through the A-A line of FIG. 1A and perpendicular to a rotation axis R in a first arrangement.
Figure 6B:
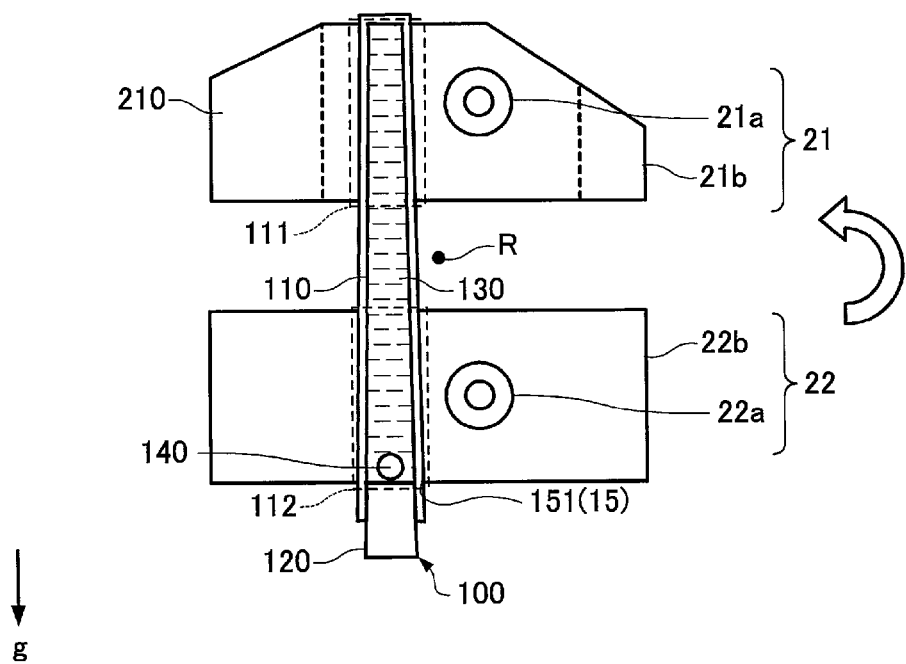
FIG. 6B is a sectional view schematically showing a section in the plane passing through the A-A line of FIG. 1A and perpendicular to the rotation axis R in a second arrangement.

FIG. 6A is a sectional view schematically showing a section in a plane passing through the A-A line of FIG. 1A and perpendicular to a rotation axis R in the first arrangement, and FIG. 6B is a sectional view schematically showing a section in the plane passing through the A-A line of FIG. 1A and perpendicular to the rotation axis R in the second arrangement. In FIGS. 6A and 6B, white arrows indicate rotation directions of the main body 10 and arrows g indicate the direction in which the gravity acts.

As shown in FIG. 6A, the first arrangement is an arrangement in which, when the attachment unit 15 is attached to the reaction container 100, the first region 111 is located in the lowermost part of the channel 110 in the direction in which the gravity acts. In the example shown in FIG. 6A, in the first arrangement, the reaction solution 140 having the higher specific gravity than that of the liquid 130 exists in the first region 111. Further, as shown in FIG. 6B, the second arrangement is an arrangement in which, when the attachment unit 15 is attached to the reaction container 100, the second region 112 is located in the lowermost part of the channel 110 in the direction in which the gravity acts. In the example shown in FIG. 6B, in the second arrangement, the reaction solution 140 having the higher specific gravity than that of the liquid 130 exists in the second region 112.

In this manner, the drive mechanism 30 rotates the attachment unit 15, the first heating unit 21, and the second heating unit 22 between the first arrangement and the second arrangement different from the first arrangement, and thereby, thermal cycling may be applied to the reaction solution 140.

According to the embodiment, by switching the arrangement of the attachment unit 15, the first heating unit 21, and the second heating unit 22, the state in which the reaction container 100 is held in the first arrangement and the state in which the reaction container 100 is held in the second arrangement may be switched. The first arrangement is the arrangement in which the first region 111 of the channel 110 forming the reaction container 100 is located in the lowermost part of the channel 110 in a direction in which the gravity acts. The second arrangement is the arrangement in which the second region 112 of the channel 110 forming the reaction container 100 is located in the lowermost part of the channel 110 in the direction in which the gravity acts. That is, when the specific gravity of the reaction solution 140 is larger than that of the liquid 130, the reaction solution 140 may be held in the first region 111 in the first arrangement and the reaction solution 140 may be held in the second region 112 in the second arrangement by the action of the gravity. The first region 111 is heated by the first heating unit 21 and the second region 112 is heated by the second heating unit 22, and thereby, the first region 111 and the second region 112 may be set at different temperatures. Therefore, while the reaction container 100 is held in the first arrangement or the second arrangement, the reaction solution 140 may be held at a predetermined temperature, and thus, the thermal cycler 1 that can easily control the heating period may be provided.

The drive mechanism 30 may rotate the attachment unit 15, the first heating unit 21, and the second heating unit 22 in opposite directions when rotating them from the first arrangement to the second arrangement and when rotating them from the second arrangement to the first arrangement. Thereby, a special mechanism for reducing twisting of wires such as the conducting wire 19 caused by rotation is unnecessary. Therefore, thermal cycler 1 suitable for downsizing may be realized. Further, it is preferable that the number of rotations for rotation from the first arrangement to the second arrangement and the number of rotations for rotation from the second arrangement to the first arrangement are less than one (the rotation angle is less than 360'). Thereby, the degree of twisting of the wires may be reduced. Alternately, as shown in FIGS. 1 and 2, the configuration in which the flange 18 can take up the conducting wire 19 may be employed.

3-1. First Specific Example of Control Method of Thermal Cycler

Figure 7:
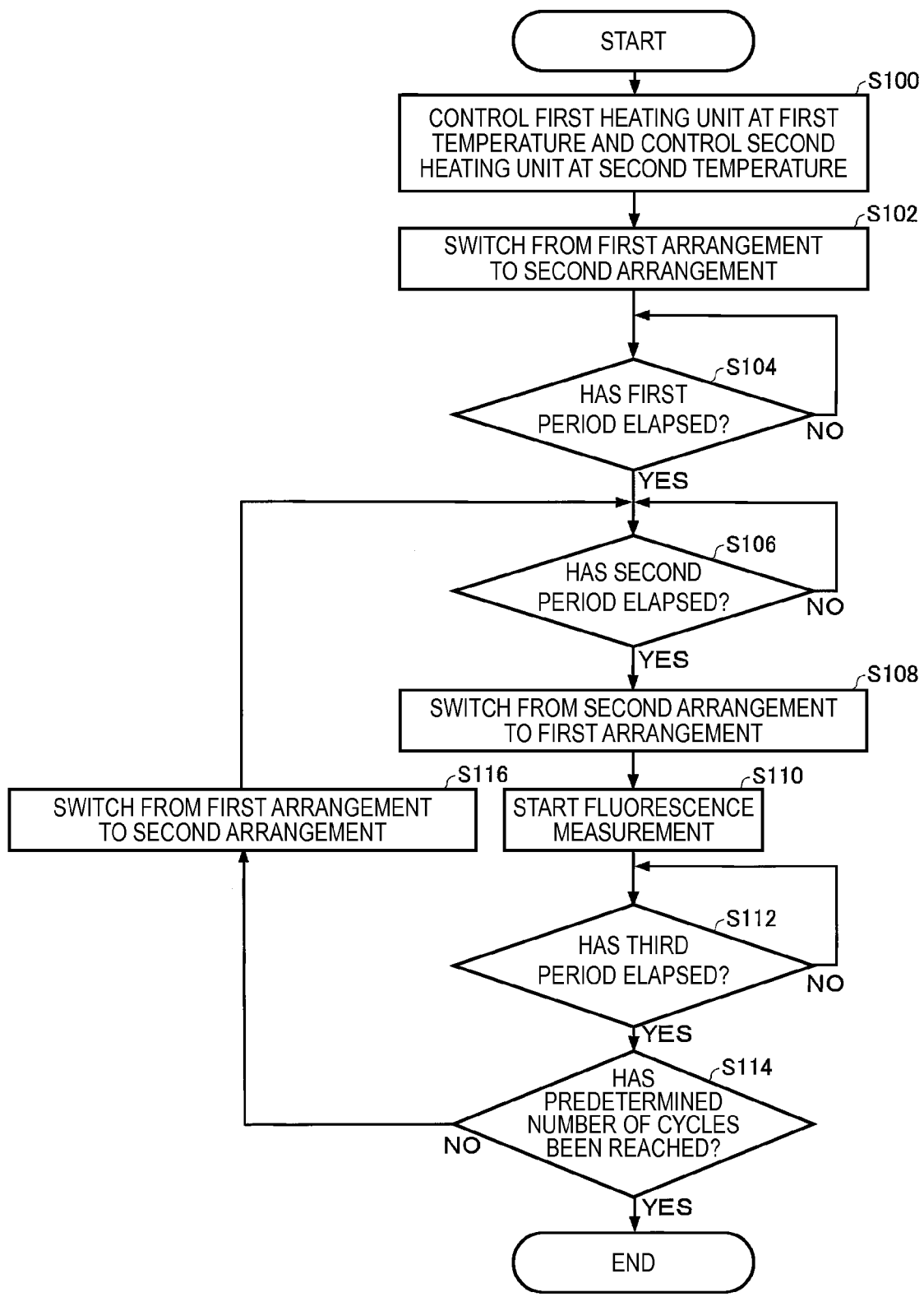
FIG. 7 is a flowchart for explanation of a first specific example of a control method of the thermal cycler 1 according to the embodiment.

Next, a first specific example of a control method of the thermal cycler 1 will be explained by taking real-time measurement in two-step temperature PCR including a hot start step as an example. Note that the reaction solution 140 contains hot start PCR enzyme and a fluorescent probe that changes intensity of light having a predetermined wavelength by complementary binding to specific DNA. FIG. 7 is a flowchart for explanation of the first specific example of the control method of the thermal cycler 1 according to the embodiment.

In FIG. 7, first, the control unit 40 controls the temperature of the first heating unit 21 at a first temperature (first processing), and controls the temperature of the second heating unit 22 at a second temperature higher than the first temperature (second processing) (step S100). In the specific example, the first temperature is the annealing and elongation temperature in PCR. "Annealing and elongation temperature in PCR" refers to a temperature depending on the type of enzyme for amplification of nucleic acid, and generally within a range from 50° C. to 70° C. In the specific example, the second temperature is the thermal denaturation temperature in PCR. "Thermal denaturation temperature in PCR" is a temperature depending on the type of enzyme for amplification of nucleic acid, and generally within a range from 90° C. to 100° C.

After step S100, the control unit 40 controls the drive mechanism 30 to switch the arrangement of the attachment unit 15, the first heating unit 21, and the second heating unit 22 from the first arrangement to the second arrangement (step S102). In thermal cycler 1 shown in FIG. 1, immediately after the reaction container 100 is attached to the attachment unit 15, the arrangement of the attachment unit 15, the first heating unit 21, and the second heating unit 22 is the first arrangement and, by performing step S102, the arrangement of the attachment unit 15, the first heating unit 21, and the second heating unit 22 is switched to the second arrangement.

Note that the reaction container 100 may be attached to the attachment unit 15 after step S100 and before step S102. Further, in the case of the configuration in which the attachment of the reaction container 100 to the attachment unit 15 is performed when the arrangement of the attachment unit 15, the first heating unit 21, and the second heating unit 22 is the second arrangement, step S102 may be unnecessary. When the arrangement of the attachment unit 15, the first heating unit 21, and the second heating unit 22 is the second arrangement, the reaction solution 140 is held in the second region 112. That is, the reaction solution 140 is held at the second temperature.

After step S102, the control unit 40 performs third processing of allowing a first period to elapse with the arrangement of the attachment unit 15, the first heating unit 21, and the second heating unit 22 being the second arrangement. Note that it is only necessary that the first heating unit 21 is at the first temperature in the third processing. That is, the third processing may be performed before the second processing or at the same time with the second processing as long as it is performed after the first processing.

More specifically, after step S102, the control unit 40 determines whether or not the first period has elapsed after step S102 is ended (step S104). In the specific example, the first period is a period necessary for activation of PCR enzyme. If the control unit 40 determines that the first period has not elapsed (if NO at step S104), the control unit 40 repeats step S104.

If the control unit 40 determines that the first period has elapsed (if YES at step S104), the control unit 40 performs fourth processing of controlling the drive mechanism 30 to switch the arrangement of the attachment unit 15, the first heating unit 21, and the second heating unit 22 from the second arrangement to the first arrangement if a second period has elapsed with the arrangement of the attachment unit 15, the first heating unit 21, and the second heating unit 22 being the second arrangement.

More specifically, first, the control unit 40 determines whether or not the second period has elapsed after step S104 is ended (step S106). In the specific example, the second period is a period necessary for denaturation in PCR. If the control unit 40 determines that the second period has not elapsed (if NO at step S106), the control unit 40 repeats step S106. If the control unit 40 determines that the second period has elapsed (if YES at step S106), the control unit controls the drive mechanism 30 to switch the arrangement of the attachment unit 15, the first heating unit 21, and the second heating unit 22 from the second arrangement to the first arrangement (step S108). When the arrangement of the attachment unit 15, the first heating unit 21, and the second heating unit 22 is the first arrangement, the reaction solution 140 is held in the first region 111. That is, the reaction solution 140 is held at the first temperature.

The reaction solution 140 is held at the second temperature in the third processing and the fourth processing, and the reaction solution 140 is held at the first temperature lower than the second temperature after the fourth processing. When the thermal cycler 1 is applied to PCR, the first temperature corresponds to the annealing and elongation temperature and the second temperature corresponds to the denaturation temperature of DNA. Generally, the temperature at which the PCR enzyme is activated is nearly equal to the denaturation temperature. Therefore, by performing the third processing, thermal cycling that enables hot start of PCR may be realized in addition to the thermal cycling of normal PCR. Further, by performing the third processing before the second processing (allowing the first time to elapse), thermal cycling including hot start may be realized without affecting the second period of the second processing.

After the third processing, the control unit 40 may control the measurement unit 50 to measure the intensity of the light having the predetermined wavelength. More specifically, after step S106, the measurement unit 50 starts fluorescence measurement (step S110). The fluorescence measurement with respect to plural reaction containers 100 may be performed by moving the measurement unit 50 on the slide 52.

By controlling the measurement unit 50 to measure the intensity of the light having the predetermined wavelength after the third processing, the intensity of the light having the predetermined wavelength emitted by the fluorescent probe binding to the DNA sequence may be measured in the period in which the reaction solution 140 is held at the annealing and elongation temperature. Therefore, the thermal cycler 1 suitable for real-time PCR may be realized.

After the fourth processing, the control unit 40 may perform fifth processing of controlling the drive mechanism 30 to switch the arrangement of the attachment unit 15, the first heating unit 21, and the second heating unit 22 from the first arrangement to the second arrangement and the forth processing repeatedly at a predetermined number of times if a third period has elapsed with the arrangement of the attachment unit 15, the first heating unit 21, and the second heating unit 22 being the first arrangement.

More specifically, first, after step S110, the control unit 40 determines whether or not the third period has elapsed after step S108 is ended (step S112). In the specific example, the third period is a period necessary for annealing and elongation in PCR. If the control unit 40 determines that the third period has not elapsed (if NO at step S112), the control unit 40 repeats step S112. If the control unit 40 determines that the third period has elapsed (if YES at step S112), the control unit 40 determines whether or not a predetermined number of cycles has been reached (step S114).

If the control unit 40 determines that the predetermined number of cycles has not been reached (if NO at step S114), the control unit 40 controls the drive mechanism 30 to switch the arrangement of the attachment unit 15, the first heating unit 21, and the second heating unit 22 from the first arrangement to the second arrangement (step S116). After step S116, steps S106 to S114 are repeated. If the control unit 40 determines that the predetermined number of cycles has been reached (if YES at step S114), the processing is ended.

The reaction solution 140 is held at the second temperature until the second period has elapsed in the second arrangement in the fourth processing, and the reaction solution 140 is held at the first temperature until the third period has elapsed in the first arrangement in the fifth processing. In this manner, by repeating the fifth processing and the fourth processing (more specifically, step S116 and steps S106 to S114), thermal cycling suitable for PCR may be performed repeatedly at a predetermined number of times.

3-2. Second Specific Example of Control Method of Thermal Cycler

Figure 8:
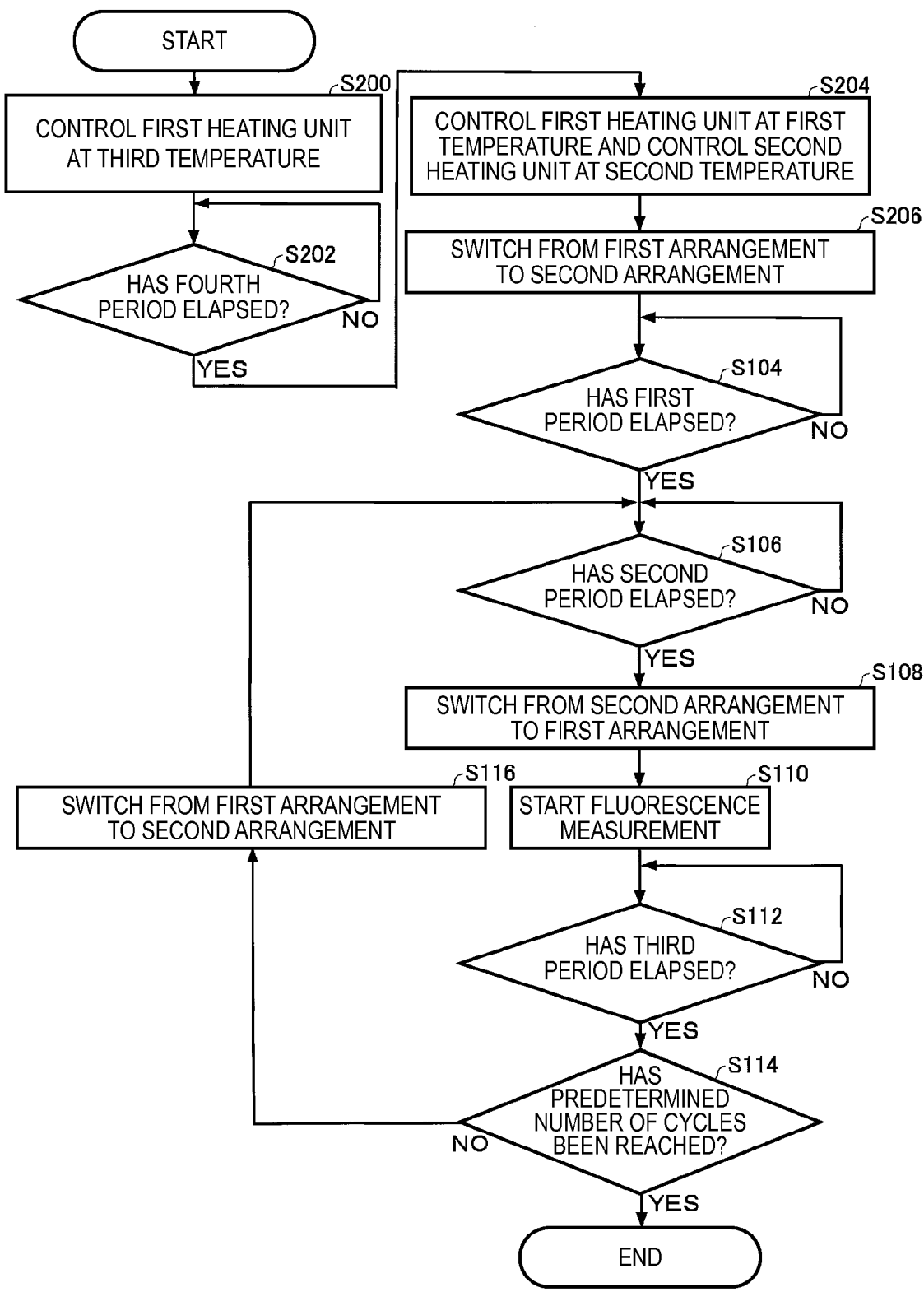
FIG. 8 is a flowchart for explanation of a second specific example of a control method of the thermal cycler 1 according to the embodiment.

Next, a second specific example of the control method of the thermal cycler 1 will be explained by taking real-time measurement in RT-PCR including a hot start step as an example. FIG. 8 is a flowchart for explanation of the second specific example of the control method of the thermal cycler 1 according to the embodiment. Note that the same steps as those in the first specific example of the control method of the thermal cycler 1 shown in FIG. 7 have the same signs, and their detailed explanation will be omitted.

In the second specific example of the control method of the thermal cycler 1, the control unit 40 performs sixth processing of controlling the first heating unit 21 at a third temperature lower than the first temperature and allowing a fourth period to elapse with the arrangement of the attachment unit 15, the first heating unit 21, and the second heating unit 22 being the first arrangement, performs seventh processing of controlling the first heating unit 21 at the first temperature and controlling the drive mechanism 30 to switch the arrangement of the attachment unit 15, the first heating unit 21, and the second heating unit 22 from the first arrangement to the second arrangement after the sixth processing and the second processing, and performs third processing after the seventh processing.

More specifically, first, the control unit 40 controls the temperature of the first heating unit 21 at the third temperature (step S200). In the specific example, the third temperature is a temperature at which reverse transcription reaction progresses by the reverse transcriptase enzyme. "The temperature at which the reverse transcription reaction progresses by the reverse transcriptase enzyme" is a temperature depending on the type of the reverse transcriptase enzyme and generally within a range from 20° C. to 70° C., and the temperature at which the reverse transcription reaction especially progresses is generally within a range from 40° C. to 50° C. Further, in the specific example, the arrangement of the attachment unit 15, the first heating unit 21, and the second heating unit 22 at the initial operation is the first arrangement. Therefore, the reaction solution 140 is held in the first region 111. That is, the reaction solution 140 is held at the third temperature.

Note that, at step S200, the control unit 40 may control the temperature of the second heating unit 22 at a temperature at which the reverse transcriptase enzyme is not deactivated. "The temperature at which the reverse transcriptase enzyme is not deactivated" is a temperature depending on the type of the reverse transcriptase enzyme, and generally within a range from 20° C. to 70° C. Further, generally, at a temperature exceeding 70° C., the reverse transcriptase enzyme is easily deactivated and deteriorated. By controlling the temperature of the second heating unit 22 at the temperature at which the reverse transcriptase enzyme is not deactivated, when the reaction container 100 is attached to the attachment unit 15, the reaction solution 140 is not subjected to a high temperature at which the reverse transcriptase enzyme is deactivated.

After step S200, the control unit 40 determines whether or not a fourth period has elapsed after step S200 is ended (step S202). In the specific example, the fourth period is a period necessary for reverse transcription reaction. If the control unit 40 determines that the fourth period has not elapsed (if NO at step S202), the control unit 40 repeats step S202. If the control unit 40 determines that the fourth period has elapsed (if YES at step S202), the control unit 40 controls the temperature of the first heating unit 21 at the first temperature and controls the temperature of the second heating unit 22 at the second temperature (step S204). The first temperature and the second temperature are the same as those in the first specific example of the control method of the thermal cycler 1 explained using FIG. 7.

After step S204, the control unit 40 controls the drive mechanism 30 to switch the arrangement of the attachment unit 15, the first heating unit 21, and the second heating unit 22 from the first arrangement to the second arrangement (step S206). Therefore, the reaction solution 140 is held in the second region 112. That is, the reaction solution 140 is held at the second temperature.

After step S206, the control unit 40 performs step S104, and the subsequent process is the same as that of the first specific example of the control method of the thermal cycler 1 explained using FIG. 7.

In this manner, by performing the seventh processing prior to the fifth processing, the reverse transcription reaction may be performed before PCR, and thus, the thermal cycler 1 suitable for RT-PCR may be realized.

Further, like the first specific example of the control method of the thermal cycler 1 shown in FIG. 7, by performing the third processing, thermal cycling that enables hot start of PCR may be realized in addition to the thermal cycling of normal PCR. Furthermore, by performing the third processing before the second processing (allowing the first period to elapse), thermal cycling including hot start may be realized without affecting the second period of the second processing.

In addition, like the first specific example of the control method of the thermal cycler 1 shown in FIG. 7, by repeating the fifth processing and the fourth processing (more specifically, step S116 and steps S106 to S114), thermal cycling suitable for PCR may be performed repeatedly at a predetermined number of times.

Further, like the first specific example of the control method of the thermal cycler 1 shown in FIG. 7, by controlling the measurement unit 50 to measure the intensity of the light having the predetermined wavelength after the third processing, the intensity of the light having the predetermined wavelength correlated with amount of specific DNA may be measured in the period in which the reaction solution 140 is held at the annealing and elongation temperature. Therefore, the thermal cycler 1 suitable for real-time PCR may be realized.

4. Working Examples

As below, the invention will be more specifically explained using working examples, however, the invention is not limited to the working examples.

4-1. First Working Example

In the first working example, an example of performing two-step temperature real-time PCR including hot start using the thermal cycler 1 will be explained.

FIG. 9 is a table showing a composition of the reaction solution 140 in the first working example. In FIG. 9, "SuperScript III Platinum" refers to "SuperScript III Platinum One-Step Quantitative RT-PCR System with ROX ("Platinum" is a registered trademark)", and contains PCR enzyme. Regarding the plasmid, samples having known copy numbers were produced by subcloning of PCR reaction products obtained using the primers shown in FIG. 10 in advance. $10^5$ plasmids were added for Sample A, $10^4$ plasmids were added for Sample B, $10^3$ plasmids were added for Sample C, and $10^2$ plasmids were added for Sample D.

FIG. 10 is a table showing base sequences of forward primers (F primers), reverse primers (R primers), and probes corresponding to influenza A virus (InfA), swine influenza A virus (SW InfA), and swine influenza H1 virus (SW H1), ribonuclease P (RNase P). All of them are the same as base sequences described in "CDC protocol of realtime RTPCR for swine influenza A (H1N1)" (World Health Organization, Revised First Edition, Apr. 30, 2009). In all of the four types of probes shown in FIG. 10, fluorescent brightness to be measured increases with amplification of nucleic acid.

The experimental procedure was as shown in the flowcharts in FIG. 7, and the first temperature was 58° C., the second temperature was 98° C., the first period was five seconds, the second period was ten seconds, the fourth period was 30 seconds, and the number of cycles of the thermal cycling processing was 50. Further, the number of reaction containers 100 attached to the attachment unit 15 was four (Sample A to Sample D).

FIG. 11 is a graph showing relationships between the number of cycles of thermal cycling processing and measured brightness in the first working example. The horizontal axis of FIG. 11 indicates the number of cycles of the thermal cycling processing and the vertical axis indicates the relative value of brightness.

As shown in FIG. 11, it is known that, regarding all of Sample A to Sample D, the brightness significantly rose as the number of cycles of the thermal cycling processing was about 20 to 35. Thereby, it is confirmed that DNA has been amplified. Further, from FIG. 11, it is confirmed that the brightness rises more significantly at the less number of cycles in the samples having the larger copy numbers of plasmid, and the number of cycles at which the brightness rises is larger as the concentration of the plasmid contained in the reaction solution 140 is higher.

As described above, it is confirmed that two-step temperature real-time PCR including hot start may be performed using the thermal cycler 1 according to the embodiment.

4-2. Second Working Example

In the second working example, an example of performing RT-PCR including hot start using the thermal cycler 1 will be explained.

Figures 12, 13:
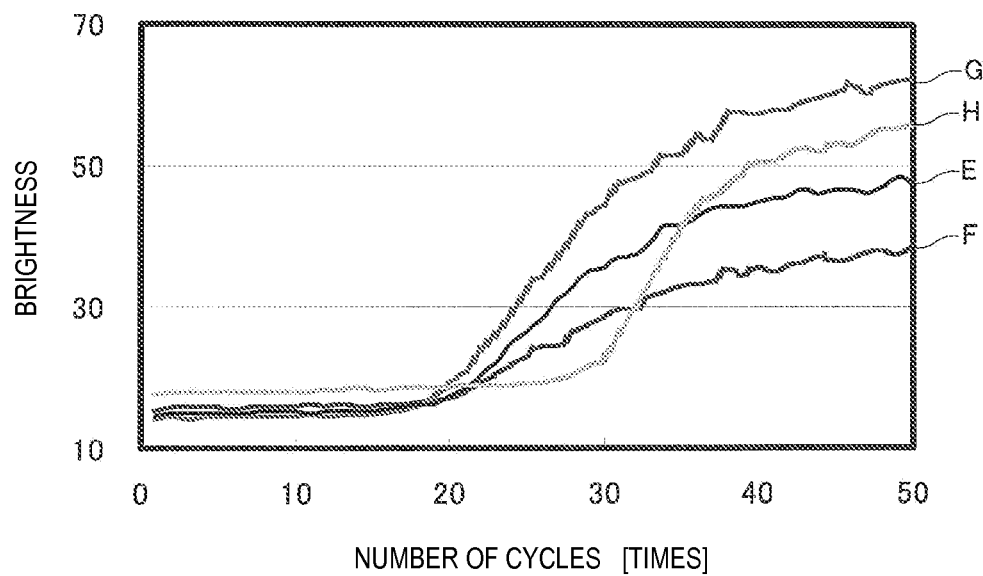
FIG. 12 is a table showing a composition of the reaction solution 140 in a second working example.
FIG. 13 is a graph showing relationships between the number of cycles of thermal cycling processing and measured brightness in the second working example.

FIG. 12 is a table showing a composition of the reaction solution 140 in the second working example. In FIG. 12, "SuperScript III Platinum" refers to "SuperScript III Platinum One-Step Quantitative RT-PCR System with ROX ("Platinum" is a registered trademark)", and contains PCR enzyme and reverse transcriptase enzyme. As RNA, RNA extracted from a human nasal cavity swab (human sample) was used. Note that, regarding the human sample, immuno chromatography was performed using a commercially available kit ("ESPLINE Influenza A&B-N) (ESPLINE is a registered trademark)", manufactured by FUJIREBIO), and the sample was positive for influenza A virus. Note that "A virus positive" in immuno chromatography does not specifically determine the influenza A virus (InfA). The base sequences of the forward primers (F primers), reverse primers (R primers), probes (Probes) in FIG. 12 are the same as the base sequences shown in FIG. 10.

The experimental procedure was as shown in the flowcharts in FIG. 8, and the first temperature was 58° C., the second temperature was 98° C., the third temperature was 45° C., the first period was five seconds, the second period was ten seconds, the third period was 60 seconds, the fourth period was 30 seconds, and the number of cycles of the thermal cycling processing was 50. Further, the number of reaction containers 100 attached to the attachment unit 15 was four (Sample E to Sample H).

Sample E contains a forward primer, a reverse primer, and a fluorescent probe corresponding to influenza A virus (InfA). Sample F contains a forward primer, a reverse primer, and a fluorescent probe corresponding to swine influenza A virus (SW InfA). Sample G contains a forward primer, a reverse primer, and a fluorescent probe corresponding to swine influenza H1 virus (SW H1). Sample H contains a forward primer, a reverse primer, and a fluorescent probe corresponding to ribonuclease P (RNase P).

FIG. 13 is a graph showing relationships between the number of cycles of thermal cycling processing and measured brightness in the second working example. The horizontal axis of FIG. 13 indicates the number of cycles of the thermal cycling processing and the vertical axis indicates the relative value of brightness.

As shown in FIG. 13, it is known that, regarding all of Sample E to Sample H, the brightness significantly rose as the number of cycles of the thermal cycling processing was about 20 to 30. Thereby, it is known that reverse-transcribed cDNA with RNA as the template has been amplified. Sample H was for an experiment of endogenous control, and it is confirmed that DNA (cDNA) derived from the human sample has been amplified because the brightness rose in Sample H. Further, it is known that all RNAs of InfA, SW InfA, SW H1 have been contained in the human sample because cDNA has been amplified in Sample E to Sample H. The result agrees with the result of immuno chromatography. Therefore, it has been confirmed that 1step RT-PCR including hot start may be performed using the thermal cycler 1 according to the embodiment.

Note that the above described embodiment and working example are just examples, and not limited to those. For example, some of the respective embodiments and the respective examples may be appropriately combined.

The invention is not limited to the above described embodiment and example, but other various modifications may be made. For example, the invention includes substantially the same configuration as the configuration explained in the embodiment (for example, a configuration having the same function, method, and result, or a configuration having the same purpose and advantage). Further, the invention includes a configuration in which an insubstantial part of the configuration explained in the embodiment is replaced. Furthermore, the invention includes a configuration that exerts the same effect or a configuration that may achieve the same purpose as that of the configuration explained in the embodiment. In addition, the invention includes a configuration formed by adding a known technology to the configuration explained in the embodiment.

The entire disclosure of Japanese Patent Application No. 2012-079766, filed Mar. 30, 2012 is expressly incorporated by reference herein.

SEQ ID NO: 1 refers to the sequence of the forward primer of InfA.

SEQ ID NO: 2 refers to the sequence of the reverse primer of InfA.

SEQ ID NO: 3 refers to the sequence of the fluorescent probe of InfA.

SEQ ID NO: 4 refers to the sequence of the forward primer of SW InfA.

SEQ ID NO: 5 refers to the sequence of the reverse primer of SW InfA.

SEQ ID NO: 6 refers to the sequence of the fluorescent probe of SW InfA.

SEQ ID NO: 7 refers to the sequence of the forward primer of SW H1.

SEQ ID NO: 8 refers to the sequence of the reverse primer of SW H1.

SEQ ID NO: 9 refers to the sequence of the fluorescent probe of SW H1.

SEQ ID NO: 10 refers to the sequence of the forward primer of RNase P.

SEQ ID NO: 11 refers to the sequence of the reverse primer of RNase P.

SEQ ID NO: 12 refers to the sequence of the fluorescent probe of RNase P.

---

What is claimed is:

1. A thermal cycler comprising:

an attachment unit for attachment of a removable reaction container including a channel filled with a reaction solution containing hot start PCR enzyme and a liquid having a specific gravity different from that of the reaction solution and being immiscible with the reaction solution, the reaction solution moving close to opposed inner walls;

a first heating unit that heats a first region of the channel when the reaction container is attached to the attachment unit, wherein the attachment unit is configured to position the reaction container so that the first heating unit heats the first region of the channel;

a second heating unit that heats a second region of the channel different from the first region when the reaction container is attached to the attachment unit, wherein the attachment unit is configured to position the reaction container so that the second heating unit heats the second region of the channel;

a drive mechanism that, when the reaction container is attached to the attachment unit, switches arrangement of the attachment unit, the first heating unit, the reaction container, and the second heating unit between a first arrangement in which a lowermost position of the channel is located within the first region and a second arrangement in which the lowermost position of the channel is located within the second region; and a control unit that controls the drive mechanism, the first heating unit, and the second heating unit, wherein the control unit is capable of first processing of controlling the first heating unit at a first temperature, second processing of controlling the second heating unit at a second temperature higher than the first temperature, third processing of allowing a first period to elapse with the arrangement of the attachment unit, the first heating unit, and the second heating unit being the second arrangement after the second processing, and fourth processing of controlling the drive mechanism to switch the arrangement of the attachment unit, the first heating unit, and the second heating unit from the second arrangement to the first arrangement if a second period has elapsed with the arrangement of the attachment unit, the first heating unit, and the second heating unit being the second arrangement after the first processing and the third processing.

2. The thermal cycler according to claim 1, wherein the control unit is capable of
fifth processing of controlling the drive mechanism to switch the arrangement of the attachment unit, the first heating unit, and the second heating unit from the first arrangement to the second arrangement and the forth processing repeatedly at a predetermined number of times if a third period has elapsed with the arrangement of the attachment unit, the first heating unit, and the second heating unit being the first arrangement after the fourth processing.

3. The thermal cycler according to claim 1, wherein the control unit is further capable of
sixth processing of controlling the first heating unit at a third temperature lower than the first temperature and allowing a fourth period to elapse with the arrangement of the attachment unit, the first heating unit, and the second heating unit being the first arrangement,
seventh processing of controlling the drive mechanism to switch the arrangement of the attachment unit, the first heating unit, and the second heating unit from the first arrangement to the second arrangement after the sixth processing and the second processing, and
third processing after the seventh processing.

4. A control method of a thermal cycler,
the thermal cycler including
an attachment unit for attachment of a removable reaction container including a channel filled with a reaction solution containing hot start PCR enzyme and a liquid having a specific gravity different from that of the reaction solution and being immiscible with the reaction solution, the reaction solution moving close to opposed inner walls,
a first heating unit that heats a first region of the channel when the reaction container is attached to the attachment unit, wherein the attachment unit is configured to position the reaction container so that the first heating unit heats the first region of the channel,
a second heating unit that heats a second region of the channel different from the first region when the reaction container is attached to the attachment unit, wherein the attachment unit is configured to position the reaction container so that the second heating unit heats the second region of the channel, and
a drive mechanism that, when the reaction container is attached to the attachment unit, switches arrangement of the attachment unit, the first heating unit, the reaction container, and the second heating unit between a first arrangement in which a lowermost position of the channel is located within the first region and a second arrangement in which the lowermost position of the channel is located within the second region,
the control method comprising:
performing first processing of controlling the first heating unit at a first temperature;
performing second processing of controlling the second heating unit at a second temperature higher than the first temperature;
performing third processing of allowing a first period to elapse with the arrangement of the attachment unit, the first heating unit, and the second heating unit being the second arrangement; and
performing fourth processing of controlling the drive mechanism to switch the arrangement of the attachment unit, the first heating unit, and the second heating unit from the second arrangement to the first arrangement if a second period has elapsed with the arrangement of the attachment unit, the first heating unit, and the second heating unit being the second arrangement after the third processing.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: InfA Forward primer

<400> SEQUENCE: 1
gatcratcct gtcacctctg ac                                              22
```

```
<210> SEQ ID NO 2
<211> LENGTH: 24
<212> TYPE: DNA
<213> ORGANISM: Artificial Sequence
<220> FEATURE:
<223> OTHER INFORMATION: InfA Reverse primer

<400> SEQUENCE: 2
agggcattyt ggacaaakcg tcta                                              24

<210> SEQ ID NO 3
<211> LENGTH: 24
<212> TYPE: DNA
<213> ORGANISM: Artificial Sequence
<220> FEATURE:
<223> OTHER INFORMATION: InfA Fluorescent probe

<400> SEQUENCE: 3
tgcagtcctc gctcactggg cacg                                              24

<210> SEQ ID NO 4
<211> LENGTH: 23
<212> TYPE: DNA
<213> ORGANISM: Artificial Sequence
<220> FEATURE:
<223> OTHER INFORMATION: SW InfA Forward primer

<400> SEQUENCE: 4
gcacggtcag cacttatyct rag                                               23

<210> SEQ ID NO 5
<211> LENGTH: 23
<212> TYPE: DNA
<213> ORGANISM: Artificial Sequence
<220> FEATURE:
<223> OTHER INFORMATION: SW InfA Reverse primer

<400> SEQUENCE: 5
gtgrgctggg ttttcatttg gtc                                               23

<210> SEQ ID NO 6
<211> LENGTH: 29
<212> TYPE: DNA
<213> ORGANISM: Artificial Sequence
<220> FEATURE:
<223> OTHER INFORMATION: SW InfA Fluorescent probe

<400> SEQUENCE: 6
cyactgcaag cccatacaca caagcagca                                         29

<210> SEQ ID NO 7
<211> LENGTH: 23
<212> TYPE: DNA
<213> ORGANISM: Artificial Sequence
<220> FEATURE:
<223> OTHER INFORMATION: SW H1 Forward primer

<400> SEQUENCE: 7
gtgctataaa caccagccty cca                                               23

<210> SEQ ID NO 8
<211> LENGTH: 24
<212> TYPE: DNA
<213> ORGANISM: Artificial Sequence
<220> FEATURE:
<223> OTHER INFORMATION: SW H1 Reverse primer
```

-continued

<400> SEQUENCE: 8
cgggatattc cttaatcctg trgc                                                  24

<210> SEQ ID NO 9
<211> LENGTH: 30
<212> TYPE: DNA
<213> ORGANISM: Artificial Sequence
<220> FEATURE:
<223> OTHER INFORMATION: SW H1 Fluorescent probe

<400> SEQUENCE: 9
cagaatatac atccrgtcac aattggaraa                                            30

<210> SEQ ID NO 10
<211> LENGTH: 19
<212> TYPE: DNA
<213> ORGANISM: Artificial Sequence
<220> FEATURE:
<223> OTHER INFORMATION: RNaseP Forward primer

<400> SEQUENCE: 10
agatttggac ctgcgagcg                                                        19

<210> SEQ ID NO 11
<211> LENGTH: 20
<212> TYPE: DNA
<213> ORGANISM: Artificial Sequence
<220> FEATURE:
<223> OTHER INFORMATION: RNaseP Reverse primer

<400> SEQUENCE: 11
gagcggctgt ctccacaagt                                                       20

<210> SEQ ID NO 12
<211> LENGTH: 23
<212> TYPE: DNA
<213> ORGANISM: Artificial Sequence
<220> FEATURE:
<223> OTHER INFORMATION: RNaseP Fluorescent probe

<400> SEQUENCE: 12
ttctgacctg aaggctctgc gcg                                                   23